United States Patent [19]

Petigara

[11] Patent Number: 5,466,818
[45] Date of Patent: Nov. 14, 1995

[54] 3-ISOTHIAZOLONE BIOCIDE PROCESS

[75] Inventor: Ramesh B. Petigara, Hatfield, Pa.

[73] Assignee: Rohm and Haas Company, Philadelphia, Pa.

[21] Appl. No.: 220,763

[22] Filed: Mar. 31, 1994

[51] Int. Cl.$^6$ ............................................. C07D 275/03
[52] U.S. Cl. ............................................. 548/213
[58] Field of Search ................................. 548/13

[56] References Cited

U.S. PATENT DOCUMENTS

| | | | |
|---|---|---|---|
| 5,028,620 | 7/1991 | Hsu | 514/372 |
| 5,068,344 | 11/1991 | Petigara et al. | 548/213 |

FOREIGN PATENT DOCUMENTS

| | | |
|---|---|---|
| 271761 | 6/1988 | European Pat. Off. . |
| 9195103 | 4/1991 | Japan . |

*Primary Examiner*—Robert Gerstl
*Attorney, Agent, or Firm*—Michael B. Fein

[57] ABSTRACT

Process for producing substantially separated 5-chloro-2-methyl-3-isothiazolone (CMI) and 2-methyl-3-isothiazolone (MI) from a mixture of their hydrochloride salts, or in a special mixture having a higher ratio of CMI to MI, comprising heating a mixture of CMI.HCl and MI.HCl for a period of time necessary to fully dissociate said CMI.HCl and form substantially pure CMI, but insufficient to fully dissociate said MI.HCl.

14 Claims, No Drawings

3-ISOTHIAZOLONE BIOCIDE PROCESS

BACKGROUND OF THE INVENTION

1. Field of the Invention

This invention is directed to preparation of 3-isothiazolone compounds.

2. Description of the Prior Art

3-Isothiazolone compounds are highly effective microbicides and have generated much commercial interest to prevent spoilage of certain aqueous and non-aqueous products caused by microorganisms.

An especially commercially important 3-isothiazolone biocide is a mixture of 5-chloro- 2-methyl-3-isothiazolone (CMI) and 2-methyl-3-isothiazolone (MI). All known processes to produce either of these compounds results in a mixture of the two. Therefore, in order to obtain either one essentially free of the other, the mixtures require separation. Until the present invention, this was both difficult and expensive.

U.S. Pat. No. 5,028,620 discloses preparing substantially pure MI by recrystallization of a crude MI.hydrochloride (HCl) salt followed by neutralization, and substantially pure CMI by partial neutralization, with pyridine, of a mixture of MI.HCl and CMI.HCl. U.S. Pat. No. 5,068,344 discloses preparing mostly pure CMI by partial neutralization of a mixture of MI.HCl and CMI.HCl with ammonia gas.

The methods taught in these U.S. patents for partially neutralizing the isothiazolone.HCl salt mixtures require the handling of an additional component (pyridine or ammonia) and provide CMI with a small amount of MI. Substantially pure MI must be obtained by other means (such as by recrystallization of the hydrochloride salt followed by neutralization).

Conventional methods of preparing the mixture of salts include, for example, cyclizing N,N'-dimethyl-3,3'-dithiopropionamide or N-methyl-3-mercaptopropionamide with a halogenating agent. The mixture of salts precipitates from the reaction mixture and can be isolated by filtration. Once isolated, the isothiazolone.HCl salts are generally washed before proceeding further. Normally, the washed mixture of CMI.HCl and MI.HCl is then neutralized with a base.

Typical halogenating agents are chlorine, sulfuryl chloride, N-chlorosuccinimide, and the like. Chlorine and sulfuryl chloride are the preferred halogenating agents.

The halogenation-cyclization is conducted in an organic solvent, typically aromatic hydrocarbons, aliphatic hydrocarbons, chlorinated aliphatic hydrocarbons, acetate esters, glycol ethers and glycol ether acetates. The preferred solvents are toluene, monochlorobenzene, ethyl acetate, ethylene dichloride, and butyl acetate.

It is well known in the art that the ratio of CMI. HCl to MI.HCl in the mixture can be varied between 4.5 and 0.02 by changing the cyclization conditions, the ratios of reactants used, and the rates of addition of the reactants.

Japanese Kokai Hei 3-095103 discloses a method of preparing a mixture of CMI and MI free of certain undesirable reaction by-products by heating a mixture of the 3-isothiazolone.HCl salts to dissociate said salts and to obtain the mixture of free base CMI and MI, rather than neutralizing with a base. This Kokai does not disclose a method for separating the individual isothiazolones.

SUMMARY OF THE INVENTION

It is an object of this invention to provide an improved process to obtain in substantially pure form CMI, or MI, or special mixtures thereof.

This is accomplished by a process for producing substantially separated CMI or MI from a mixture of their HCl salts, or a special mixture of CMI and MI which is higher in CMI:MI ratio than in the starting HCl salt mixture, comprising preparing a mixture of CMI.HCl and MI.HCl as a slurry in an organic solvent; and heating said starting salt mixture for a controlled period of time sufficient to fully dissociate said CMI.HCl and form substantially pure CMI, but insufficient to fully dissociate said MI.HCl.

DETAILED DESCRIPTION OF THE PREFERRED EMBODIMENT

The process of the invention comprises forming a slurry of the mixture of CMI.HCl and MI.HCl salts in an organic solvent and heating the slurry to selectively crack, i.e., dissociate, the CMI.HCl salt, either leaving the MI.HCl salt essentially intact as an insoluble solid, or only dissociating a desired portion. The free base CMI and any MI which is dissociated from its salt dissolve(s) in the organic solvent. The mixture is then filtered to provide essentially pure MI.HCl as a solid. The filtrate is then stripped of the organic solvent to provide essentially pure CMI or a special mixture of CMI and MI at a desired ratio which is higher than the ratio of CMI.HCl to MI.HCl in the starting mixture.

If substantially pure MI is the only desired product, a mixture of salts which is as rich as possible in MI.HCl should be used.

The isolated MI.HCl salt can be neutralized by a variety of methods, for example by reslurrying in a variety of solvents and then neutralized with an organic base such as pyridine and triethylamine, or with ammonia, which is the preferred base. The resulting precipitate, base.HCl, is removed by filtration. Removal of the solvent will provide MI as the free base. Alternatively, the MI.HCl salt can be reslurried and dissociated by heating the slurry, followed by removal of the solvent to provide substantially pure MI. When dissociating the MI.HCl, it is preferred that the slurry be dilute, less than 10% solids, and preferably less than 5% solids.

If it is desired to obtain a special mixture as defined above, rather than separate CMI and MI, the mixture of salts can be slurried as described above and heated to fully dissociate the CMI.HCl but only partially dissociate the MI.HCl. The ratio of the isothiazolones will depend upon the starting ratio of the mixture of the HCl salts, the temperature at which the salts are dissociated, and on the duration of the dissociation step. Due to the process of preparing the HCl salt mixture, the maximum practical ratio of CMI.HCl:MI.HCl in the mixture is about 4.5. By the process of this invention, greater ratios of CMI:MI (at least 4, up to 99) can be obtained.

The solvents useful in the dissociation step are acetate esters, such as ethyl acetate and butyl acetate; chlorinated aliphatic hydrocarbons, such as methylene dichloride, ethylene dichloride, propylene dichloride, and chloroform; aromatic hydrocarbons, such as toluene; and chlorinated aromatic hydrocarbons, such as monochlorobenzene. The preferred solvents are ethyl acetate, butyl acetate, methylene dichloride, ethylene dichloride, propylene dichloride, and chloroform. Ethyl acetate, methylene dichloride, ethylene dichloride and chloroform are especially preferred. Ethyl acetate is the most preferred.

The temperature for the selective dissociation of the isothiazolone.HCl salts is least about 35° C. The preferred temperature is from about 35° to about 85° C. It is further preferred that the solvent be refluxing or distilling during the dissociation step. The dissociation step can also be done at reduced pressure. At temperatures above about 85° C., it is preferred to perform the dissociation step at reduced pressure. If the solvent is distilled, fresh solvent must periodically be added to maintain the initial concentration of the slurry throughout the dissociation step.

By substantially pure CMI is meant CMI having a purity of at least 95% and containing less than 1% of MI. By substantially pure MI is meant MI having a purity of at least 95% and containing less than 0.4% CMI. It is preferred that MI have a purity of 98%.

Either CMI or MI can be formulated in a variety of solvents, such as water or glycols, such as propylene glycol, dipropylene glycol, and the like. It is also known that in certain solvents it is necessary to add stabilizers to prevent decomposition of CMI or MI. Suitable stabilizers include metal nitrates, such as magnesium nitrate; trialkyl orthoesters, such as triethyl orthoformate; anhydrides; epoxides; antimony salts; olefins; and the like.

EXAMPLE 1

Preparation of Isothiazolone.HCl salts

Into a one-liter, 4-necked, round bottom flask equipped with a mechanical stirrer, thermometer, gas dispersion tube, and dry ice condenser with nitrogen inlet adapter, was placed methyl-3-mercaptopropionate (504.7 g, 4.20 mol). The vessel was purged with nitrogen and the liquid was cooled to 10° C. Monomethylamine (163.0 g, 5.25 mol) was added through the gas dispersion tube with stirring at 10°–20° C. over a one hour period. Following the addition, the mixture was stirred at 20° C. for 20 hours to complete the reaction. Unreacted monomethylamine and the methanol by-product was then removed under reduced pressure (100 mmHg). The resultant mixture was then further reduced on a rotary evaporator to give crude N-methyl-3-mercaptopropionamide (500.8 g, 100% yield).

A one-liter, 5-necked, jacketed resin kettle was equipped with an agitator, fritted glass dispersion tube, thermometer, condenser attached to an off-gas scrubber, and a feed line for N-methyl-3-mercaptopropionamide slurry. The jacket was connected to a temperature control bath for coolant circulation. The cooling system maintained the reaction temperature at 25°–30° C. The flask was charged with 59.5 g of ethyl acetate. A slurry (398.9 g) of N-methyl-3-mercaptopropionamide in ethyl acetate (31%) was added to the flask over a 55 minute period at a rate of 7.1 g/minute. Concurrently, 220 g of $Cl_2$ were added at a rate of 4.0 g/minute. Following the complete addition of N-methyl- 3-mercaptopropionamide and $Cl_2$, the reaction mixture was filtered, and the cake washed with ethyl acetate to yield a mixture of CMI.HCl and MI.HCl.

EXAMPLE 2

Selective Dissociation of CMI.HCl

To a one-liter, jacketed, resin flask equipped with an overhead agitator, thermometer, condenser, and a temperature control bath, was added 60 g of an 81:19 mixture of CMI.HCl and MI.HCl, prepared according to Example 1, in 340 g of ethyl acetate. The slurry (containing 15% solids) was heated to 78°–80° C. for 2 hours. After heating, the reaction mixture was cooled to room temperature, the slurry was filtered and the solid was washed with ethyl acetate. The filtrate was stripped to yield 42 g of substantially pure CMI. The ratio of CMI:MI in the filtrate was 99.2/0.8.

The solid contained 96.4% MI.HCl and only 1.4% CMI.HCl.

EXAMPLE 3

Dissociation of both CMI.HCl and MI.HCl

Example 2 was repeated using a more dilute slurry (9%) of the isothiazolone.HCl salt mixture. The slurry was heated at 78°–80° C. until most of the solids had disappeared. At the end of this period, the mixture was filtered and the filtrate removed to provide a mixture of CMI and MI in a ratio of 80:20, essentially the same ratio as in the starting isothiazolone.HCl salt mixture.

EXAMPLE 4

Selective Dissociation of both CMI.HCl and MI.HCl

To a 500 ml jacketed flask equipped with an overhead agitator, thermometer, condenser fitted with a drying tube, and a temperature control bath, was added 31.3 g of an 82:18 mixture of CMI.HCl and MI.HCl, prepared according to Example 1, in 468 g of methylene dichloride. The slurry (6.25% solids) was heated to 36.5°–37° C. Aliquots of the mother liquor were taken at various time points, stripped and analyzed for the amount of free base isothiazolones. After 16 hours heating, the reaction mixture was cooled to room temperature, the slurry was filtered and a small amount of the solid was washed with methylene dichloride. The filtrate was stripped and the resulting material was analyzed for free base isothiazolone content. The results are shown in Table 1.

TABLE 1

| Dissociation of Isothiazolone.HCl Salt Mixture in Methylene Dichloride | | | |
|---|---|---|---|
| Time (hrs) | CMI (wt %) | MI (wt %) | CMI:MI |
| 0* | 62.0* | 13.3* | 82.3:17.7* |
| 1 | 95.3 | 1.4 | 98.5:1.5 |
| 2 | 95.3 | 2.5 | 97.5:2.5 |
| 4 | 92.5 | 4.3 | 95.5:4.5 |
| 8 | 87.1 | 7.9 | 96.1:3.9 |
| 12 | 89.0 | 7.4 | 92.3:7.7 |
| 15 | 88.7 | 7.7 | 92.0:8.0 |
| 16 | 84.0 | 9.3 | 90.0:10.0 |

*These data represent the amounts in the starting isothiazolone.HCl salt mixture.

The data in Table I clearly show that CMI.HCl can be selectively dissociated from the mixture of the two isothizolone.HCl salts, or both salts may be dissociated to yield a special mixture of the free base isothiazolones, CMI and MI in any ratio higher in CMI than the ratio of salts in the starting mixture.

EXAMPLE 5

Selective Dissociation of both CMI.HCl and MI.HCl

To a 500 ml jacketed flask equipped with an overhead agitator, thermometer, condenser fitted with a drying tube, and a temperature control bath, was added 50.6 g of a 73:27 mixture of CMI.HCl and MI.HCl, prepared according to Example 1, in 349.4 g of ethyl acetate. The slurry (10% solids) was heated to reflux and the solvent partially distilled (rate=20 ml/min) while replenishing the kettle with fresh ethyl acetate. Aliquots of the mother liquor were taken at various time points. These were filtered and the solids washed with ethyl acetate and analyed for isothiazolone content. The filtrates from these aliquots were stripped and analyzed for the amount of free base isothiazolones. After 7 hours of refluxing, essentially all of the solids had dissolved. The reaction mixture was cooled to room temperature and then the solvent was stripped under reduced pressure. The results are shown in Table 2.

TABLE 2

Dissociation of Isothiazolone.HCl Salt Mixture in Ethyl Acetate

| | Filtrate | | | Solids | | |
|---|---|---|---|---|---|---|
| | Wt % | | | Wt % | | |
| Time (hrs) | CMI | MI | CMI:MI | CMI.HCl | MI.HCl | CMI.HCl:MI.HCl |
| —* | — | — | — | 53.9 | 18.0 | 73:27 |
| 0** | 86.9 | 1.2 | 98.6:1.4 | 37.2 | 32.4 | 53.4:46.6 |
| 1 | 90.0 | 2.8 | 97.0:3.0 | 0.31 | 64.7 | 0.5:99.5 |
| 2 | 82.0 | 10.8 | 88.4:11.6 | 0.29 | 65.1 | 0.4:99.6 |
| 3 | 77.2 | 14.6 | 83.9:16.1 | 0.42 | 65.2 | 0.6:99.4 |
| 4 | 76.5 | 18.2 | 80.5:19.5 | — | — | — |
| 5 | 72.8 | 20.0 | 78.4:21.6 | — | — | — |
| 6 | 73.6 | 20.8 | 78.0:22.0 | — | — | — |
| 7 | 69.4 | 25.7 | 73.0:27.0 | — | — | — |

*These data are from the solid at the time of slurry preparation.
**The 0 hour sample was taken at the start of reflux.

The data in Table 2 clearly show a surprisingly high degree of selectivity favoring CMI.HCl dissociation during the first hour of reflux, giving essentially pure CMI containing only a small amount of MI. Importantly, it is possible to obtain a special CMI:MI mix with any desired ratio from about 99:1 to the starting ratio of 73:27, depending on the duration of this dissociation step.

EXAMPLE 6

Isolation of Substantially Pure MI.HCl

A mixture of CMI.HCl and MI.HCl was prepared according to Example 1 except that the cyclization reaction was carried out at 45°–50° C. and 384.9 g of a 31% solution of N-methyl-3-mercaptopropionamide in ethyl acetate were added concurrently with 138.5 g $Cl_2$ over a 2 hour period to the flask charged with 132.5 g of ethyl acetate. At the end of this time, the reaction mixture was filtered and the cake washed with ethyl acetate to yield a mixture of CMI.HCl and MI.HCl in a 9:91 ratio.

Example 2 was repeated using 400g of a 20% solids slurry of this 9:91 mixture of CMI.HCl and MI.HCl in ethyl acetate. The slurry was heated at reflux for 1 hour. The mixture was allowed to cool to room temperature and filtered. The wet cake was washed with 100 g of ethyl acetate and dried to give substantially pure MI.HCl (87.4 g) containing only a trace amount of CMI.HCl in a CMI:MI ratio of 0.2:99.8.

EXAMPLE 7

Isolation of Substantially Pure MI

Substantially pure MI was prepared by slurrying the MI.HCl from Example 6 in ethyl acetate (20% solids) and neutralizing with ammonia. The solids were filtered and the filtrate was concentrated under reduced pressure (50° C./20 mmHg) to provide substantially pure MI (99.0%) containing only a small amount of CMI (0.12%). The ratio of CMI:MI was 0.4:99.6.

EXAMPLE 8

Isolation of Substantially Pure MI

Substantially pure MI.HCl was dissociated to yield MI according to the procedure of Example 2. The MI.HCl (4.4 g) from Example 6 was slurried in 345.6 g of ethyl acetate (1.25% solids) and heated under reflux for 2 hours and then subjected to distillation for 30 minutes. The mixture was then allowed to cool and the remaining solids were filtered. The filtrate was concentrated under reduced pressure (50° C./20 mmHg) to give an oil. The oil was substantially pure MI containing only 0.21% CMI.

EXAMPLE 9

Isolation of Substantially Pure MI.HCl

Example 6 was repeated except using a mixture of CMI.HCl and MI.HCl in a 2:98 ratio, to obtain essentially the same ratio of CMI:MI. This example has the advantage of sacrificing only a small amount of CMI.

We claim:

1. A process for producing either (a) substantially separated CMI and MI from a mixture of their HCl salts, or (b) a special mixture of CMI and MI which is higher in CMI:MI ratio than in said mixture of their HCl salts, comprising preparing a mixture of CMI.HCl and MI.HCl as a slurry in an organic solvent selected from the group consisting of acetate esters, chlorinated aliphatic hydrocarbons, aromatic hydrocarbons, and chlorinated aromatic hydrocarbon; and refluxing said slurry for a controlled period of time sufficient to fully dissociate said CMI.HCl, but insufficient to fully dissociate said MI.HCl.

2. Process according to claim 1 comprising separating the resultant dissociated CMI from said MI.HCl by filtration, and then neutralizing said MI.HCl to form substantially pure MI.

3. Process according to claim 1 wherein said solvent is selected from the group consisting of ethyl acetate, butyl acetate, methylene dichloride, ethylene dichloride, propylene dichloride, and chloroform.

4. Process according to claim 1 wherein said period of time is less than one hour.

5. Process according to claim 1 wherein said MI.HCl and CMI are separated by filtering out the insoluble MI.HCl and then removing solvent from the filtrate to obtain substantially pure CMI.

6. Process according to claim 1 wherein a stabilizer for said CMI is added to said separated CMI or to said special mixture of CMI and MI, or to a solution thereof.

7. Process according to claim 1 wherein said organic solvent is ethyl acetate and said period of time is about 0.5 to 1.5 hours.

8. Process according to claim 1 wherein comprising refluxing said mixture at about 35° C. to 85° C.

9. Process according to claim 1 wherein said heating is under reduced pressure.

10. Process according to claim 1 wherein said mixture of CMI.HCl and MI.HCl has a ratio of CMI.HCl:MI.HCl of at least about 2.3, and wherein a special mixture is prepared wherein said ratio of CMI:MI is about 4 to 99.

11. Process according to claim 10 wherein said ratio of CMI.HCl:MI.HCl is about 2.3 to 4.5, and said ratio of CMI:MI is higher, and is about 4 to 99.

12. Process according to claim 1 comprising separating the resultant dissociated CMI from said MI.HCl by filtration, reslurrying said MI.HCl in an organic solvent at less than 10.% solids, and refluxing the resultant slurry of MI.HCl to substantially dissociate said MI.HCl, resulting in a solution of MI.

13. Process according to claim 12 wherein the solids content of said MI.HCl in said resultant slurry is less than about 5%.

14. Process of claim 12 wherein the ratio of CMI.HCl to MI.HCl in said mixture is about 0.02 to 0.12.

* * * * *